United States Patent [19]

Krezanoski et al.

[11] 3,954,644

[45] *May 4, 1976

[54] FLEXIBLE CONTACT LENS CLEANING, STORING, AND WETTING COMPOSITIONS

[75] Inventors: Joseph Z. Krezanoski; John C. Petricciani, both of Los Altos, Calif.

[73] Assignee: Flow Pharmaceuticals, Inc., Palo Alto, Calif.

[ * ] Notice: The portion of the term of this patent subsequent to May 6, 1992, has been disclaimed.

[22] Filed: July 9, 1973

[21] Appl. No.: 377,430

Related U.S. Application Data

[60] Division of Ser. No. 279,800, Aug. 11, 1972, Pat. No. 3,882,036, which is a continuation-in-part of Ser. No. 148,993, June 1, 1971, abandoned, which is a continuation-in-part of Ser. No. 724,600, April 26, 1968, abandoned.

[52] U.S. Cl................................ 252/106; 424/78; 424/317; 424/320; 424/329
[51] Int. Cl.²......................................... C11D 3/48
[58] Field of Search............. 252/106, 107; 424/78, 424/320, 329, 317

[56] References Cited
UNITED STATES PATENTS

| | | | |
|---|---|---|---|
| 2,703,777 | 3/1955 | Feinstein et al. | 424/329 X |
| 2,921,885 | 1/1960 | Bouchal | 424/320 X |
| 3,052,604 | 9/1972 | Davis et al. | 424/329 X |
| 3,171,752 | 3/1965 | Rankin | 424/329 X |
| 3,183,152 | 5/1965 | Szekely et al. | 424/78 |
| 3,240,709 | 3/1966 | Rankin | 424/329 X |
| 3,539,520 | 11/1970 | Cantor et al. | 252/107 X |

*Primary Examiner*—Edward A. Miller
*Attorney, Agent, or Firm*—Finnegan, Henderson, Farabow & Garrett

[57] ABSTRACT

A contact lens cleaning, storing and wetting solution is provided for cleaning, storing and wetting flexible silicone contact lenses. The solution comprises a poly (oxyethylene)- poly (oxypropylene) block copolymer having a molecular weight between about 1900 and 15,500, a water solubility in excess of about 10 grams per 100 ml., a cloud point in 1 percent aqueous solution above about 30°C., and a Foam Height in excess of 30 mm; a microbial growth inhibitor, such as benzalkonium chloride; purified water; and a sufficient amount of at least one essentially neutral, water-soluble compatible salt to provide a solution salt content equivalent to about 0.5 to 1.8 percent sodium chloride. The solution can also contain disodium or trisodium ethylenediamine tetraacetate and a polymeric viscosity building agent, if desired.

16 Claims, No Drawings

FLEXIBLE CONTACT LENS CLEANING, STORING, AND WETTING COMPOSITIONS

This application is a division of application Ser. No. 279,800, filed Aug. 11, 1972 and now U.S. Pat. No. 3,882,036, entitled CONTACT LENS CLEANING, STORING AND WETTING COMPOSITIONS. Application Ser. No. 279,800 is a continuation-in-part of application Ser. No. 148,993, filed June 1, 1971, entitled CLEANING AND GERMICIDAL COMPOSITIONS, now abandoned. Application Ser. No. 148,993 is a continuation-in-part of application Ser. No. 724,600, filed Apr. 26, 1968 entitled CLEANING AND GERMICIDAL COMPOSITIONS, now abandoned.

This invention relates to various contact lens cleaning, storing and wetting compositions, and more particularly to compositions for treating soft contact lenses, such as flexible silicone contact lenses and polyhydroxylated alkyl methacrylate contact lenses and to compositions for use with conventional hard polymethylmethacrylate lenses.

The proper care of contact lenses can be viewed as requiring three necessary steps. First, after removal from the eye the lenses must be cleaned to physically remove foreign matter from their surfaces. Second, the lenses must be sterilized. Finally, the lenses must be prepared for insertion into the eye.

In the past, contact lenses have been made of hard polymethacrylates. Proper care of these lenses has required that they be stored in specially developed cleaning and storage solutions to maintain them in good order when not in use. The storage solutions are formulated to sterilize the lenses during the lenses' storage. Many of these cleaning and storage solutions contain chlorobutanol as a preservative which acts to preserve the sterility of the solution.

When ready for use, the hard contact lenses have beem immersed in contact lens wetting solutions. The wetting solutions are designed to condition and prepare the contact lenses for wetting by natural tear fluid, and their use has made the wearing of contact lenses more tolerable, particularly in the newly initiated patient, by reducing irritation of the corneal epithelium. Prior art contact lens wetting solutions have usually contained polyvinyl alcohol as a wetting agent. These wetting solutions also have often contained chlorobutanol as a preservative.

Recently, a new type of contact lens known as a soft lens has been developed. Soft lenses can be divided into two broad catagories, namely hydrophilic lenses and hydrophobic lenses. The care of each of these lenses presents special and different problems.

Hydrophobic contact lenses are usually based on elastic and flexible silicone rubber (polysiloxane), and are generally made from cross-linked dimethyl polysiloxane which is commonly known as Antifoam A. A typical preparation of a hydrophobic silicone contact lens is disclosed in U.S. Pat. No. 3,228,741, which is hereby incorporated by reference and comprises forming a mixture of a suitable polymerization catalyst, up to 40 percent silica as a filler, and the siloxane polymer, and then molding and curing with heat to further polymerize the polysiloxane by cross-linking to produce the finished clear lens. Clinical testing of flexible silicone rubber lenses has created a need for cleaning, storing and wetting solutions that can be effectively used with these lenses.

In testing the commercially available solutions designed for conventional hard polymethylmethacrylate contact lenses, it has been found that they are not adequate and in some instances detrimental to the successful use of flexible silicone contact lenses. For example, it has been found that polyvinyl alcohol, the wetting ingredient in many wetting solutions for conventional hard polymethylmethacrylate lenses, is not an effective wetting agent for silicone lenses. It has also been found that the preservative chlorobutanol present in many commercially available solutions designed for hard polymethylmethacrylate lenses is absorbed and concentrated by silicone lenses. This ability of the silicone elastomer to concentrate chlorobutanol could ultimately change the physical and chemical properties of the lenses to make them ineffective in providing visual correction.

Moreover, patients experimentally wearing flexible silicone rubber lenses stored in a chlorobutanol containing storage solution have complained of discomfort. This was found to be directly associated with the high concentrations of chlorobutanol in the silicone lenses thus treated.

The highly hydrophobic nature of the silicone elastomer has prevented their uniform and effective cleaning and wetting by all available conventional cleaners and wetting agents. Thus, various generic classes of organic compounds have been screened including cellulose derived gums, polyvinylpyrrolidone polymers, polyvinyl alcohol with varying degrees of acetylation, polysaccharides, lanolin derived nonionic surfactants, ethoxylated sorbitol anhydrides, and various cationic, anionic and nonionic detergents, but to date none have been found acceptable.

Hydrophilic soft contact lenses are hydrated gel lenses which can be prepared by copolymerizing hydrophilic organic monomers having an olefinic double bond with a small amount of a cross-linking agent usually having two polymerizable, olefinic double bonds. These lenses are usually based on polyhydroxylated alkyl methacrylates and contain a polyhydroxylated alkyl methacrylate, such as polyhydroxyethyl methacrylate, cross-linked with, for example, a hydroxyethyl dimethacrylate. Usually, there is about one (1) cross-linking molecule for every 200 monomer units. By comparison, the conventional hard contact lens consists of polymethylmethacrylate cross-linked with hydroxyethyl dimethacrylate. The absence of a hydrophilic OH group in conventional hard lenses accounts for the tremendous difference in behavior of the two materials.

Hydrated gel lenses can contain the following materials: (1) hydroxyethylmethacrylate (HEMA) or its analogues, (2) ethylene-geycol dimethacrylate (EGMA) or its analogues, (3) polymethylmethacrylate (PMMA) or its analogues, (4) polyvinylpyrrolidone (PVP), (5) traces of the respective monomers, (6) traces of inhibitors such as hydroquinine, (7) traces of catalysts such as benzyl peroxide, and (8) water. A more detailed description of hydrated gel lenses is found in U.S. Pat. Nos. 2,976,576; 3,220,960; 3,361,858; 3,408,429; 3,496,254; and 3,499,862, which patents are hereby incorporated by reference.

Soft contact lenses of the hydrated gel type have a number of properties which complicate their effective care. For example, the hydrophilic OH groups of the lenses attract and hold large amounts of water in the plastic, and this leads to difficulties in cleaning and sterilizing the lenses. Further difficulties in caring for hydrated gel lenses occur because these lenses complex and concentrate chlorobutanol, benzalkonium chloride, thimerosal, phenylmercuric nitrate and other preservatives found in solutions for conventional lenses. Generally, these preservatives are inactivated in the complexed state. Also, if concentrated preservatives are released too rapidly at the cornea, they may cause chemical burns. Thus, solutions and cleaners now available for conventional hard lenses cannot be used with gel lenses.

The methods currently used in caring for hydrophilic gel lenses generally include the following: (1) boiling in saline; (2) treating with 3 percent hydrogen peroxide; (3) rinsing with "sterile" saline; and (4) storing in sterilizing solutions. Each of these methods, however, have numerous disadvantages. For example, boiling in saline kills pathogens, but does not kill spores. Another disadvantage of boiling is that it is not convenient for patients to carry the boiling devices with them wherever they go. Further, proteins and other materials may be denatured and deposited on or in the lens matrix if the lenses are not adequately cleaned prior to boiling. The effects of boiling on soluble or water dispersible proteins are similar to the coagulating and insolubilizing effects of heat on egg whites. Thus, once these deposits are allowed to accumulate on the lenses, substantially more effort is required to clean them.

Commercial hydrogen peroxide has satisfactory germicidal activity, but its use also has a number of disadvantages. Commercial hydrogen peroxide has a pH of about 3 and it is therefore necessary to treat the lenses with sodium bicarbonate solution to neutralize the high acidity before the lenses can be worn safely. A major concern, however, is the ever present possibility that the patient will forget to neutralize and dilute the hydrogen peroxide with sodium bicarbonate solution prior to inserting the lens. Further, the cleaning action of hydrogen peroxide is no better than that achieved with water or isotonic salt solutions. In fact, hydrogen peroxide, because of its oxidative chemical reactivity, can denature and precipitate proteins.

Rinsing lenses with unpreserved and supposed sterile saline solution delivered from a large multiple dose bottle, is far from adequate in sterilizing lenses.

Experimental isotonic sterilizing solutions of two basic types are currently available. One solution contains chlorhexidine gluconate 0.005 percent as the active ingredient. Another solution contains 0.001 percent thimerosal, 0.05 percent EDTA, and chlorhexidine 0.005 percent. Both of these solutions have drawbacks. Thus, chlorhexidine is not only inactivated by many peptides, proteins and fatty substances of natural origin bearing a net negative charge, but causes the formation of insoluble precipitates. To a lesser extent, this same phenomenon may occur when the negatively charged thimerosal ion reacts with proteins bearing a net positive charge. Further, neither solution is ideal when prolonged wearing comfort, complete sterility reliance and lack of allergic response are considered. Although these solutions have been tested for their cleaning efficiency, they fall significantly short of accomplishing this objective when used on a routine basis. This is not surprising since neither of these solutions was specifically formulated for this purpose.

The necessity for proper cleaning of the new hydrophilic gel lenses is readily apparent. Throughout the development phase of these lenses, there has been no effective preparation in clinical testing and none has been formulated or developed specifically for routine cleaning of gel lenses.

Any residual protein remaining in or on the lens may readily inactivate even the best germicidal agents and serve as growth medium for a variety of microorganisms. While many germicidal chemicals, in appropriate concentrations, demonstrate sterilization of fresh lenses, these same chemicals do not necessarily sterilize a lens worn repeatedly and improperly cleaned. Thus, there is a continuing need for an effective cleaner for hydrated gel lenses which would permit the lenses to be cleaned before they are placed in a germicidal environment to minimize the likelihood of overwhelming the germicide.

It has now been found that certain members of the polyoxypropylene-polyoxyethylene class of block copolymers are effective in accomplishing both cleaning, storing and wetting of flexible silicone lenses and that these same members in combination with sorbic acid as a preservative are effective in providing cleaning of hydrophilic gel lenses.

Accordingly, the present invention provides a sterile, aqueous cleaning, storing and wetting solution for flexible silicone rubber contact lenses containing as the active wetting and cleaning ingredient 0.01–30 percent of a polyoxyethylene-polyoxypropylene block copolymer having a molecular weight between about 1900 and 15,500, a water solubility in excess of about 10 grams per 100 ml., a cloud point in a 1 percent aqueous solution above about 30° C, and a Foam Height in excess of 30 mm. The solution also contains a sufficient amount of a germicidal composition compatible with silicone lenses to preserve the sterility of the solution; a sufficient amount of at least one water-soluble, compatible salt to provide a solution salt content equivalent to about 0.5 to 1.8 percent sodium chloride, and balance water.

The above composition for cleaning, storing and wetting flexible silicone rubber lenses can contain a viscosity builder such as hydroxyethyl cellulose and this combination of ingredients provides an all purpose composition for cleaning, storing and wetting conventional hard, polymethacrylate lenses.

The present invention also provides a new cleaning composition for hydrated gel lenses which comprises 0.01 to 40 percent of a polyoxyethylene-polyoxypropylene block copolymer having a molecular weight between about 1900 and 15,500, a water solubility in excess of about 10 grams per 100 ml, a cloud point in a 1 percent aqueous solution above about 30°C, a Foam Height in excess of 30 mm, and sorbic acid as a germicidal ingredient to preserve the sterility of the composition. The composition also includes a sufficient amount of at least one water soluble compatible salt to provide a solution having a tonicity compatible with human tear fluid, and a balance of water. This cleaning composition can also be used to clean conventional hard polymethacrylate lenses and flexible silicone rubber soft contact lenses.

The invention consists in the novel compositions, methods, products and improvements shown and described. It is to be understood that both the foregoing general description and the following detailed description are exemplary and explanatory but are not restrictive of the invention.

The silicone lens cleaning, storing and wetting solution of this invention is an aqueous solution. The inert nature of water, and the fact that it is a good solvent for the other ingredients of the present solution, together with its ready availability, make it the desirable base material for this solution. The water used in the solution is preferably purified by distillation, filtration, ion-exchange or the like.

The silicone lens cleaning, storing and wetting solution of this invention preferably contains a compatible, polymeric, viscosity-building agent. The viscosity-building agent must, of course, be water soluble. Either cellulosic polymers or natural gums are satisfactory viscosity-building agents for the solutions.

Thus, natural gums such as guar gum, gum tragacanth, gelatin and water-soluble starch derivatives can be used. Water-soluble cellulosic polymers such as hydroxyethyl cellulose, methyl cellulose, hydroxypropyl cellulose, carboxymethyl cellulose, and the like are preferred viscosity-building agents, with hydroxyethyl cellulose and methyl cellulose being considered optimum.

The viscosity-building agent used in the solution of this invention provides lens cushioning and corneal comfort, while avoiding stickiness of the eyelid and granulation on the eyelashes. These desirable properties are best achieved through the use of hydroxyethyl cellulose or methyl cellulose as the viscosity-building agents.

Sufficient amounts of the viscosity-building agent are added to the solution to produce a cleaning and wetting solution having a viscosity of about 15 to 750 cps at 25°C. A viscosity of about 60 cps at 25°C is considered optimum.

The use of medium viscosity cellulosic polymers, which are readily available commercially, is beneficial in achieving the desired viscosity in the silicone rubber contact lens cleaning, storing and wetting solution. Exemplary of such medium viscosity polymers are M grade hydroxyethyl cellulose available from Hercules, Inc., under the trademark Natrosol. A 2 percent solution of this polymer at 25°C has a Brookfield viscosity of about 4500–6500. It is to be understood, however, that cellulosic polymers of widely varying viscosities can be used satisfactorily in the wetting solutions of this invention. Thus, Natrosol polymers of viscosity grades H, G and J from Hercules, Cellosize WP4400 from Union Carbide Corp. and various other commercially available hydroxyethyl cellulose polymers can be used. The preferred grade of methyl cellulose for use in these cleaning and wetting solutions is methyl cellulose U.S.P. XVII, which can be obtained commercially from Dow Chemical Co., Union Carbide and others.

Highly desirable silicone contact lens cleaning, storing and wetting solutions are produced by the incorporation of 0.05 to 1.0 percent of the viscosity-building agents in the solution.

The silicone rubber contact lens cleaning, storing and wetting solution of this invention contains a germicide, designed to prevent or inhibit microbial growth. The inclusion of such germicides is particularly important where multi-dose bottles of the solution are prepared. The germicides prevent bacteria from contaminating the solution after its container has been opened and initial use made of a portion of the solution. The germicidal ingredient used in the silicone lens treating composition of this invention is bacteridical and imparts a sterilizing capability to the composition so that it can be used as a soaking solution for contact lens storage.

Quaternary germicides are preferred, particularly benzalkonium chloride. This compound has minimal potential for toxicity and irritation at the germicidally effective strengths incorporated in the present solution, and it does not present a significant problem of percutaneous absorption. Benzalkonium chloride is an alkyl substituted dimethylbenzylammonium chloride in which the alkyl substituents are a mixture of $C_8$ to $C_{18}$ alkyl radicals.

Other well known germicidal agents compatible with flexible silicone lenses such as thimerosal sodium, cetylpyridinium chloride, and benzethonium chloride can be substituted wholly or partially for the preferred benzalkonium chloride preservative. Sorbic acid, NF XIII can also be used as a germicidal ingredient in the silicone lens solution of this invention. In order to maintain sterility of the product during use, the preferred quaternary or organic mercurial germicide should be present in an amount of about 0.001 to 0.03 percent of the overall solution, and preferably in concentrations of from 0.004 to 0.02 percent. The optimum concentration is about 0.01 percent. A preferred concentration for sorbic acid NF XIII is between about 0.01 and 0.5 percent of the overall solution.

The silicone contact lens cleaning, storing and wetting solution of this invention can optionally contain about 0.01 to 2 percent of a salt of ethylenediaminetetraacetic acid, and preferably contains disodium or trisodium ethylenediaminetetraacetate. The former is commonly known as sodium edetate.

Trisodium edetate serves as a combination germicide and chelating agent and its inclusion in the present composition at levels of 0.01 to 2 percent maintains the pH of the composition at alkaline levels, i.e., above pH 7.0, and preferably at from pH 8 to 9. The alkalinity of the solution enhances the germicidal activity of quaternary germicides such as benzalkonium chloride, and also enhances the solvent activity of the composition for proteins, fats, and mucopolysaccharides that accumulate on the plastic surfaces of contact lenses from contact with body tissues and fluids during normal use.

Specifically, trisodium ethylenediaminetetraacetate enhances the germicidal action of benzalkonium chloride against certain gram negative organisms including *Pseudomonas aeruginosa*, *Alcaligenese faecalis*, and *Escherichia coli*. The enhancement of germicidal activity is particularly significant in the alkaline environment.

The alkalinity of the compositions of this invention produced by the use of trisodium ethylenediaminetetraacetate also improves the chelating ability and therefore the water softening characteristics of the trisodium ethylenediaminetetraacetate, a property that is desirable in a cleaning and germicidal composition for contact lenses. These chelating and water softening properties of the solution are important because divalent and trivalent cations often present in body fluids can reduce the germicidal potency of benzalkonium chloride by blocking the surfaces of the lenses to be cleaned.

Disodium ethylenediamine tetraacetate also provides additional protection against pseudomonal contamination, and also act as a chelating or water softening agent. The sodium edetate ties up divalent and trivalent cations often present in the water, thereby preventing undesirable precipitates from forming and ultimately fogging the contact lens surface. Other salts of ethylenediaminetetraacetate, such as the dipotassium salt can be used in the present invention.

The silicone rubber contact lens cleaning, storing and wetting solutions of this invention preferably have a pH between about 5 and 9. The solutions are not buffered, however, and therefore do not resist conversion to a normal pH by tear fluid which usually has a pH of about 7.4. The elimination of buffers from the present solution is desirable because strongly buffered solutions can cause temporary stinging and discomfort of the eye on contact with the solution or a contact lens wetted with it.

A sufficient amount of at least one essentially neutral water-soluble compatible salt is incorporated in the silicone lens treating solutions of this invention to provide a solution salt content equivalent to about 0.5 to 1.8 percent sodium chloride. The silicone contact lens cleaning, storing and wetting solutions of the present invention are generally formulated to be isotonic with human serum and tear fluid, that is, they are formulated to contain the same salt concentration as that present in the serum and tear fluid of the user. The normal tonicity of human serum and tear fluid is 0.9 percent (9.0 grams of sodium chloride per liter of fluid), and normally, isotonic solutions contain approximately 0.9 percent sodium chloride, or other salt or mixture of salts having a tonicity approximately equivalent to that of 0.9 percent sodium chloride.

The tonicity of the solution, however, can be as low as 0.5 or as high as 1.8. Thus, it is sometimes desirable to provide a mildly hypertonic silicone lens cleaning, storing and wetting solution, that is, a solution having a salt concentration and hence an osmotic pressure higher than that of the serum and tear fluid of the contact lens wearer. Mildly hypertonic solutions can be used in the present invention, and the teachings of U.S. Pat. No. 3,549,747 relating to the formulation of such solutions are hereby incorporated by reference. Thus, the silicone lens treating solutions of the present invention can have a tonicity equivalent to about 1.5 percent sodium chloride as taught in U.S. Pat. No. 3,549,747 and can have a maximum tonicity equivalent to about 1.8 percent sodium chloride.

As will be apparent to those of ordinary skill in the art any soluble salt or mixture of salts compatible with ocular tissue can be used to provide the desired tonicity. Preferably, sodium chloride, potassium chloride, or mixtures thereof, are used to provide the desired tonicity. It is to be understood, however, that one or more essentially neutral, water soluble alkali metal salts can be substituted in whole or in part for the sodium or potassium chloride in the solutions of this invention. Thus, other alkali metal halides, such as sodium bromide, potassium fluoride or potassium bromide can be used. Other salts, such as sodium sulfate, potassium sulfate, sodium nitrate, sodium phosphate, potassium nitrate or potassium phosphate can also be used. The tonicity of the silicone lens treating solutions of this invention however, is stated in terms of sodium chloride, and when such other salts are used, they should be present in amounts equivalent to the tonicity of about 0.5 to 1.8 percent sodium chloride solutions.

In accordance with the invention, the silicone lens treating composition contains a physiologically-acceptable and chemically compatible polyoxypropylene-polyoxyethylene block copolymer. This copolymer is the primary wetting and cleaning ingredient of the composition.

The products sold under the trademark "Pluronic" by Wyandotte Chemical Corp. are a series of closely related block polymers that may be generally classified as polyoxypropylene-polyoxyethylene condensates terminating in primary hydroxyl groups. They are formed by the condensation of propylene oxide onto a propylene glycol nucleus followed by the condensation of ethylene oxide onto both ends of the polyoxypropylene base. The polyoxyethylene hydrophilic groups on the ends of the molecule are controlled in length to constitute anywhere from 10 to 80 percent by weight of the final molecule. This series of products may be represented empirically by the formula:

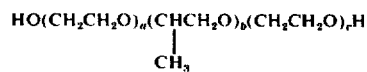

where $a$ and $c$ are statistically equal. These polyol block copolymers are nonionic surface-active agents.

In accordance with the invention, certain members of this series of block polymers having a particular combination of physical and chemical properties have been found to be effective cleaning and wetting agents for flexible silicone contact lenses. Thus, the polyoxypropylene-polyoxyethylene block copolymers useful in the present invention have a molecular weight between about 1900 and 15,500, and a water solubility is in excess of about 10 grams per 100 ml.

Additionally, the block copolymers useful in the present invention must have a cloud point in 1 percent aqueous solution above about 30°C, and a Foam Height in excess of 30 mm. The cloud point is the temperature at which a waxy solid material appears in solution as a 1 percent aqueous solution of the block copolymer is cooled. The Foam Height is the value obtained on a Dynamic Foam Tester operated at a temperature of 120°F using a 0.1 percent polyol concentration at a flow rate of 400 ml./min, for 10 minutes.

An additional requirement of the block copolymers used in the silicone lens treating solution of the present invention is that they be physiologically-acceptable so that no adverse reaction occurs when the solution comes in contact with human tissue or fluids. Thus, aqueous solutions of the block copolymers must be inert when they are tested for ocular tolerance in human and rabbit eyes.

Among the polyoxypropylene-polyoxyethylene block copolymers satisfying the above conditions are the following Pluronic copolymers: Pluronic F-68, Pluronic L-44, Pluronic L-62, Pluronic L-64, Pluronic F-108, and Pluronic F-127. Pluronics F-68, L-44, L-62, L-64, F-108 and F-127 when tested in concentrations of 10% – 25% show only minimal or no eye irritation. The following Table 1 lists the properties of a number of the block copolymers that can be used in the present invention.

TABLE 1

| PLURONIC | Average Molecular Weight | Cloud Point in 1% Aq. Solution, °C. | Solubility in Water | FOAMING PROPERTIES Foam Heights (mm) at flow of 400 ml/min. |
|---|---|---|---|---|
| 1) L44 | 2200 | 65 | >10 | 360 |
| 2) L62 | 2500 | 32 | >10 | 35 |
| 3) L64 | 2900 | 58 | >10 | >600 |
| 4) F68 | 8350 | >100 | >10 | >600 |
| 5) F108 | 15,500 | >100 | >10 | 425 |
| 6) F127 | 11,500 | >100 | >10 | 250 |

To perform the important dual cleaning and wetting functions of the silicone lens treating solutions of this invention, the block copolymers should be present in an amount of from 0.01 to 30 percent of the solution, and preferably are present in an amount of 0.01 to 5 percent of the solution. At these concentrations, the block copolymers effectively remove proteins, fats, and mucopolysaccharides that accumulate on the silicone lens surfaces when they come in contact with body tissues and fluids. The block copolymers also act to help maintain the germicidal storage container in a generally clean state. Importantly, the block copolymers also act as a wetting agent in the solution so that the flexible silicone contact lenses can be immediately inserted in the eye of the user upon their removal from the solution without using a separate wetting solution.

The silicone lens treating solutions of the present invention are thus used for cleaning, storing, wetting and preconditioning flexible silicone contact lenses and make these lenses a safe and functional prosthesis for correcting visual abberations.

When the above compositions for cleaning, storing, and wetting silicone lenses contain a viscosity builder, such as hydroxyethyl cellulose, they also have utility as an all purpose solution for cleaning, storing and wetting conventional hard polymethacrylate lenses.

In accordance with another aspect of the invention, a cleaning solution is provided for cleaning hydrophilic gel lenses and comprises 0.01 to 40 percent of a poly-(oxyethylene)-poly(oxypropylene) block copolymer, a sufficient amount of a germicidal composition containing sorbic acid to preserve the sterility of the solution, a sufficient amount of at least one water soluble compatible salt to provide a solution having a tonicity compatible with human tear fluid, and a balance of water.

The block copolymers useful in this cleaning solution are the identical block copolymers that are used in the cleaning, storing and wetting solution for silicone lenses as described above and thus have the same combination of physical and chemical properties that are described above in connection with the cleaning, storing and wetting solution for silicone lenses. Thus, the block copolymers have a molecular weight between about 1900 and 15,500, and a water solubility in excess of about 10 grams per 100 ml. Additionally, the block copolymers useful in the present invention must have a cloud point in 1 percent aqueous solution above 30°C, and a Foam Height in excess of 30mm.

The cleaning composition can contain from about 0.01 to 40 percent of the block copolymer and preferably contains 12 to 20 percent with 15 percent being presently preferred. A preferred block copolymer is sold under the trademark "Pluronic F-127" by the Wyandotte Chemical Corp.

The sorbic acid is incorporated into the cleaning composition hydrophilic gel lenses in an amount between 0.01 and 0.5 percent of the overall composition, and preferably in an amount of 0.1 to 0.2 percent. The sorbic acid has a bactericidal effect and importantly is not concentrated by the hydrophilic gel lenses, thus making it an ideal germicidal agent for use with hydrophilic gel lenses.

The hydrophilic gel lens cleaning composition preferably contains about 0.01 –1.0 percent of a salt of ethylene-diaminetetra-acetic acid, such as disodium EDTA or trisodium EDTA. These salts serve as combination germicide and chelating agents. The sorbic acid used in the cleaning composition has greater effectiveness at lower pH values and accordingly the cleaning composition is desirably maintained at a pH of 7 or below, with a pH of 6 being presently preferred. Preferably, disodium edetate is used in combination with the sorbic acid because trisodium edetate maintains the composition at a higher pH range. Disodium edetate is not concentrated by hydrophilic gel lenses and thus is a useful ingredient in cleaning solutions for such lenses. By itself, disodium edetate has a bacteriostatic effect, and in combination with sorbic acid provides a cleaning solution having good bactericidal properties.

A sufficient amount of at least one essentially neutral water-soluble compatible salt is incorporated in the hydrophilic gel lens cleaning solution of this invention to provide a tonicity compatible with human tear fluid. Preferably, the tonicity of the solution is isotonic with human serum and tear fluid, and thus has a tonicity of approximately 0.9 percent, although deviations of plus or minus 20 percent (0.72–1.08 percent tonicity) can be made. Any greater deviation would cause undesirable differences in osmotic pressure between the natural fluids of the eye and the solution. Preferably, a mixture of sodium chloride and potassium chloride is used to achieve the desired tonicity.

A typical regimen for a hydrophilic gel lens contact wearer would call for cleaning the lenses immediately after they are removed from the eye with the cleaning composition of this invention, followed by water rinsing of the lenses. The lenses would then be subjected to boiling in normal saline in accordance with conventional procedures to asepticize them. The lenses would be hermetically kept in the normal saline until ready for use. The boiling fluid should contain a protective preservative to provide chemical resterilizing capacity in the event that the seal in the boiling container fails. The presence of a preservative should also be helpful if the container is opened to expose the lenses to non-sterile air for any significant period of time prior to wearing the lens.

The cleaning composition of this invention for hydrated gel lenses markedly improves the cleanliness and preserves the optical clarity of the lenses. Further, studies indicate that patients who have previously experienced discomfort and red eyes associated with the wearing of their hydrophilic gel lenses have exhibited marked improvement when a cleaning step with the cleaner of this invention is incorporated in their daily care regimen.

Although the above cleaning composition is specifically formulated for use with hydrophilic gel lenses, the present invention has discovered that this composition can also be used as a cleaner for silicone rubber contact lenses and for hard polymethacrylate contact lenses. When used for these purposes, the tonicity of the solution can be varied over a wider range of 0.5–1.8 percent. Although the silicone lens cleaning, storing, and wetting solution described above is satisfactory in obtaining cleaning of the silicone lenses, a still more effective procedure for the care of these lenses would be to first use the cleaning solution for the hydrophilic gel lenses, followed by water rinsing and then storage and wetting in the silicone lens cleaning, storing and wetting solution.

For a clearer understanding of the invention, specific examples of it are set forth below. These examples are merely illustrative and are not to be understood as limiting the scope and underlying principles of the invention in any way. All parts and percentages referred to in this specification and the appended claims are by weight in terms of unit volume of solution unless otherwise specifically indicated. Thus, a benzalkonium chloride content of 0.1 percent in the solution is equivalent to one gram of benzalkonium chloride per liter of solution.

EXAMPLE 1

A cleaning, storing and wetting solution for flexible silicone contact lenses is prepared having the following composition:

| | |
|---|---|
| Polyoxypropylene-polyoxyethylene condensate (Pluronic F-68) | 0.5% |
| Benzalkonium chloride | 0.01% |
| Hydroxyethylcellulose (medium viscosity grade) | 0.25% |
| NaCl | 0.75% |
| KCl | 0.2% |
| Trisodium ethylenediaminetetraacetate | 0.10% |
| Distilled Water, Q.S. | 100% |

This solution is rapidly germicidal on silicone contact lenses and these contact lenses can be stored indefinitely in the solution without the accumulation of deposits on the lenses.

The solution of this example wets flexible silicone contact lenses so that they can be inserted on the cornea without eye irritation or tissue intolerance upon being taken out of the solution and without use of any other wetting solution.

This solution is tested clinically on six patients wearing flexible silicone lenses. The subjective response of these patients is that the solution is better than anything they had previously tried.

The germicidal and bactericidal activity of the cleaning and wetting solution of this example is tested against the following organisms:

1. Staph. aureus
2. Strep. pyogenes
3. E. coli
4. Pseud. aeruginosa
5. C. albicans All tests are conducted in duplicate. Twenty four hour broth cultures of the organisms are centrifuged at 3000 rpm for 20 minutes. The supernatant is decanted and the remaining pellet resuspended in phosphate buffered saline (PBS). Each bacterial suspension in the amount of 0.2 ml. is added to 3.8 ml. samples of the wetting and cleaning solution of this example and to 3.8 ml. samples of a control solution of PBS. The resulting suspensions represent a 1/20 dilution of the test reagent and are held at room temperature and assayed at 5, 30 and 60 minutes. The assay procedure consists of serially diluting by ten fold the various bacterial suspension in Tryptic soy broth containing neutralizing buffer and Tween 80. The results of these tests are set forth in the following Table 1:

Table 1

| | Cleaning, Wetting and Storing Solution of this Example | | |
|---|---|---|---|
| | Time of Exposure of Organisms to Test Solution | | |
| Organism | 5 min. | 30 min. | 60 min. |
| (1) Staph. aureus | negative | negative | negative |
| (2) Strep. pyogenes | negative | negative | negative |
| (3) E. coli | negative | negative | negative |
| (4) Pseud. aeruginosa | negative | negative | negative |
| (5) C. albicans | negative | negative | negative |
| | Control Assay | | |
| (1) Staph. aureus | $10^8$org/ml | $10^8$org/ml | $10^8$org/ml |
| (2) Strep. pyrogenes | $10^5$org/ml | $10^5$org/ml | $10^5$org/ml |
| (3) E. coli | $10^8$org/ml | $10^8$org/ml | $10^8$org/ml |
| (4) Pseud. aeruginosa | $10^8$org/ml | $10^8$org/ml | $10^8$org/ml |
| (5) C. albicans | $10^6$org/ml | $10^6$org/ml | $10^6$org/ml |

Table 1 shows that the cleaning, storing and wetting solution is bactericidal even in the presence of large numbers of organisms.

The cleaning, storing and wetting solution of this example is also tested for eye irritancy. Two Silicon silicone rubber contact lenses (Mueller Welt Contact Lenses, Inc., Chicago, Ill) are placed in 5 ml. of the cleaning and wetting solution and soaked for 4 weeks at room temperature. At the end of the soaking period, the lenses are removed from the solution. This solution is then tested by the standard six-rabbit eye irritation test.

Six female albino New Zealand rabbits are used. Both eyes of each animal are examined before testing. The test solution is placed in one eye of each animal by gently pulling the lower lid away from the eyeball to form a cup into which the test substance is dropped. The lid is then gently held together for 1 second. The other eye, remaining untreated, serves as a control. The dose for each rabbit is 0.1 ml.

The eyes are examined and the grade of ocular reaction is recorded at 24, 48 and 72 hours. Reading of reactions is facilitated by the use of ophthalmoscope.

The reactions are scored by using the "Illustrated Guide for Grading Eye Irritation by Hazardous Substances" as suggested in Section 191.12 of the Federal Hazardous Substances Act.

None of the rabbits tested show a positive reaction during the experimental period and thus the cleaning and wetting solution of this example is considered not to be an eye irritant.

In addition to being used as a cleaning, storing and wetting solution for flexible silicone lenses, the composition of this example is also an effective cleaning, storing and wetting solution for conventional hard polymethylmethacrylate lenses.

EXAMPLE 2

Another cleaning, storing and wetting solution for flexible silicone contact lenses in accordance with this invention is prepared in this example. The solution has the following composition:

| | |
|---|---|
| Polyoxypropylene-polyoxyethylene condensate (Pluronic F-127) | 2.0% |
| Benzalkonium chloride | 0.013% |
| NaCl | 0.9% |
| Distilled Water, Q.S. | 100% |

This composition is an effective germicidal, cleaning and wetting solution for flexible silicone contact lenses, and these lenses can be stored in it indefinitely.

EXAMPLE 3

Another cleaning, storing and wetting composition for flexible silicone contact lenses is prepared having the following composition:

| | |
|---|---|
| Polyoxyethylene-polyoxypropylene condensate (Pluronic F-108) | 0.1% |
| Thimerosal sodium | 0.005% |
| Disodium EDTA | 0.05% |
| KCl | 1.2% |
| Deionized Water, Q.S. | 100% |

This composition is an effective germicidal, cleaning and wetting solution for flexible silicone contact lenses, and these lenses can be stored in it indefinitely.

EXAMPLE 4

A cleaning composition for flexible hydrophilic gel contact lenses in accordance with this invention is prepared with the following ingredients:

| | |
|---|---|
| Polyoxyethylene-polyoxypropylene condensate (Pluronic F-127) | 18% |
| Sorbic Acid N.F.XIII | 0.1% |
| Disodium EDTA | 0.5% |
| Sodium Chloride | 0.65% |
| Potassium Chloride | 0.20% |
| Deionized Water Q.S. | 100% |

This composition forms a gel above 70°F while below this temperature it remains a viscous liquid and is an excellent cleaner for hydrophilic gel lenses made from hydroxyethylmethacrylate copolymerized with polyvinylpyrrolidine and various other agents.

In addition this composition can be used for cleaning flexible silicone lenses and conventional hard polymethacrylate lenses.

The invention in its broader aspects is not limited to the specific details shown and described, but departures may be made from such details within the scope of the accompanying claims without departing from the principles of the invention and without sacrificing its chief advantages.

What is claimed is:

1. An aqueous solution suitable for cleaning, storing and wetting flexible silicone contact lenses which comprise:
   a. 0.01 to 30 percent of a poly(oxyethylene)-poly(oxypropylene) block copolymer having a molecular weight between about 1900 and 15,500, a water solubility in excess of about 10 grams per 100 ml., a cloud point in 1 percent aqueous solution above about 30°C and a Foam Height in excess of 30 mm.;
   b. a sufficient amount of germicidal composition compatible with silicone flexible lenses to preserve the sterility of the solution;
   c. a sufficient amount of at least one water-soluble, salt compatible with occular tissue to provide a solution salt content equivalent to about 0.5 to 1.8 percent sodium chloride; and
   d. balance water.

2. The composition of claim 1 which contains about 0.01 to 5 percent of said poly(oxyethylene)-poly(oxypropylene) block copolymer.

3. The composition of claim 1 which also contains a cellulosic viscosity-building agent.

4. The composition of claim 1 in which the water-soluble salt is selected from the group consisting of NaCl, KCl or mixtures thereof.

5. The composition of claim 1 in which the germicidal composition is selected from benzalkonium chloride, thimerosal sodium, sorbic acid, or a combination of benzalkonium chloride or thimerosal sodium or sorbic acid with a salt of ethylenediaminetetraacetate.

6. A composition for cleaning flexible polyhydroxylated hydrophilic gel contact lenses which comprises:
   a. 0.01 to 40 percent of a poly(oxyethylene)-poly(oxypropylene) block copolymer having a molecular weight between about 1900 and 15,500, a water solubility in excess of about 10 grams per 100 ml., a cloud point in 1 percent aqueous solution above about 30°C and a Foam Height in excess of 30 mm.;
   b. a sufficient amount of a germicidal composition compatible with polyhydroxylated hydrophilic gel lenses and containing sorbic acid to preserve the sterility of the composition;
   c. a sufficient amount of at least one water-soluble, salt compatible with occular tissue to provide a composition having a tonicity compatible with human tear fluid; and
   d. balance water.

7. The composition of claim 6 which contains about 15 percent of said poly(oxyethylene)-poly(oxypropylene) block copolymer.

8. The composition of claim 6 wherein the water soluble salt is a mixture of sodium chloride and potassium chloride.

9. The composition of claim 8 wherein the concentration of sodium chloride is about 0.65 percent and the concentration of potassium chloride is about 0.20 percent.

10. The composition of claim 9 wherein the germicidal composition comprises a mixture of sorbic acid and disodium ethylenediaminetetraacetate.

11. The composition of claim 10 wherein the concentration of sorbic acid is from about 0.01 to 0.5 percent and the concentration of disodium ethylenediaminetetraacetate is from about 0.01 to 1.0 percent.

12. The composition of claim 10 wherein the concentration of sorbic acid is about 0.1 percent and the concentration of disodium ethylenediaminetetraacetate is about 0.5 percent.

13. The composition of claim 11 which contains about 12–20 percent of a poly(oxyethylene)-poly(oxypropylene) block copolymer.

14. A composition for cleaning flexible silicone contact lenses and hard polymethyacrylate lenses which comprises:
   a. 0.01 to 40 percent of a poly(oxyethylene)-poly(oxypropylene) block copolymer having a molecular weight between about 1900 and 15,500, a water solubility in excess of about 10 grams per 100 ml., a cloud point in 1 percent solution above about 30°C and a Foam Height in excess of 30 mm.;
   b. a sufficient amount of a germicidal composition compatible with the lenses and containing sorbic acid to preserve the sterility of the solution;
   c. a sufficient amount of at least one water-soluble salt compatible with occular tissue to provide a composition having a solution salt content equivalent to about 0.5–1.8 percent sodium chloride; and
   d. balance water.

15. The composition of claim 14 wherein the germicidal composition includes disodium ethylenediaminetetraacetate.

16. The composition of claim 15 wherein the concentration of sorbic acid is from about 0.01 to 0.5 percent and the concentration of disodium ethylenediaminetetraacetate is from about 0.01 to 1.0 percent.

* * * * *